United States Patent [19]

Leiner et al.

[11] Patent Number: 5,554,100
[45] Date of Patent: Sep. 10, 1996

[54] ARTHROSCOPE WITH SHIM FOR ANGULARLY ORIENTING ILLUMINATION FIBERS

[75] Inventors: Dennis C. Leiner, Dublin, N.H.; William G. Peck, Rochester, N.Y.; Theodorus W. A. van den Berg, Beek en Donk, Netherlands; Jörg Brambring, Eindhoven, Netherlands; Willem J. Voormolen, Mierlo, Netherlands

[73] Assignees: United States Surgical Corporation, Norwalk, Conn.; U.S. Philips Corporation, New York, N.Y.

[21] Appl. No.: 217,502

[22] Filed: Mar. 24, 1994

[51] Int. Cl.$^6$ ............................. A61B 1/07; G02B 6/00
[52] U.S. Cl. ..................... 600/182; 600/129; 600/171; 600/920; 385/117
[58] Field of Search ..................... 128/4–10; 385/117, 385/902, 43; 600/182, 170, 171, 128, 129, 920

[56] References Cited

U.S. PATENT DOCUMENTS

| | | |
|---|---|---|
| 2,699,770 | 1/1955 | Fourestier et al. .................. 128/6 |
| 3,089,484 | 5/1963 | Hett . |
| 3,257,902 | 6/1966 | Hopkins . |
| 3,297,022 | 1/1967 | Wallace . |
| 3,556,085 | 1/1971 | Takahashi . |
| 4,025,155 | 5/1977 | Imai . |
| 4,036,218 | 7/1977 | Yamashita et al. . |
| 4,076,018 | 2/1978 | Heckele . |
| 4,138,192 | 2/1979 | Yamasita . |
| 4,140,364 | 2/1979 | Yamashita et al. . |
| 4,148,550 | 4/1979 | MacAnally . |
| 4,148,551 | 4/1979 | MacAnally . |
| 4,165,917 | 8/1979 | Yamasita et al. . |
| 4,168,882 | 9/1979 | Hopkins . |
| 4,173,392 | 11/1979 | Ekinaka et al. . |
| 4,267,828 | 5/1981 | Matsuo . |
| 4,273,110 | 6/1981 | Groux . |
| 4,300,812 | 11/1981 | Nakahashi . |
| 4,354,730 | 10/1982 | Bel . |
| 4,369,768 | 1/1983 | Vukovic . |
| 4,385,810 | 5/1983 | Hamou . |
| 4,414,962 | 11/1983 | Carson . |
| 4,461,281 | 7/1984 | Carson . |
| 4,501,477 | 2/1985 | Sunaga . |
| 4,545,652 | 10/1985 | Hoogland . |
| 4,569,334 | 2/1986 | Ohshiro . |
| 4,572,201 | 2/1986 | Kondo et al. . |
| 4,575,195 | 3/1986 | Hoogland . |
| 4,576,147 | 3/1986 | Hashiguchi . |
| 4,615,333 | 10/1986 | Taguchi . |
| 4,624,243 | 11/1986 | Lowery et al. . |
| 4,655,557 | 4/1987 | Takahashi . |

(List continued on next page.)

FOREIGN PATENT DOCUMENTS

| | | |
|---|---|---|
| 3838168 | 10/1988 | Germany . |
| 544422 | 1/1977 | U.S.S.R. . |
| 686725 | 9/1979 | U.S.S.R. . |
| 683721 | 9/1979 | U.S.S.R. . |
| WO93/15647 | 8/1993 | WIPO . |

*Primary Examiner*—Joe Cheng
*Assistant Examiner*—John P. Leubecker

[57] ABSTRACT

A disposable rigid arthroscope having an inclined angle of view includes a frame member, an outer tube member extending distally from the frame member, an inner lens tube member eccentrically disposed within the outer tube member, an optical system disposed within the inner lens tube member and having a mechanism for altering the field of view of the optical system with respect to the optical axis and an illumination system including a plurality of optical fibers. The optical fibers of the illumination system are oriented by a shim member to emit light in the general direction of the inclined field of view to sufficiently illuminate the surgical field. The shim member includes opposed side edges that are angularly oriented relative to the optical axis and a proximal end portion extending along an inner periphery of the outer tube member to define a major cross-sectional dimension approximating a maximum inner dimension of the outer tube member.

32 Claims, 9 Drawing Sheets

U.S. PATENT DOCUMENTS

| | | |
|---|---|---|
| 4,660,982 | 4/1987 | Okada . |
| 4,664,486 | 5/1987 | Landre et al. . |
| 4,676,606 | 6/1987 | Takahashi . |
| 4,684,224 | 8/1987 | Yamashita et al. . |
| 4,693,568 | 9/1987 | Takahashi . |
| 4,697,577 | 10/1987 | Forkner . |
| 4,699,463 | 10/1987 | D'Amelio et al. . |
| 4,704,007 | 11/1987 | Landre et al. . |
| 4,723,843 | 2/1988 | Zobel . |
| 4,727,859 | 3/1988 | Lia . |
| 4,730,909 | 3/1988 | Takahashi . |
| 4,742,818 | 5/1988 | Hughes et al. . |
| 4,747,661 | 5/1988 | Ohkuwa . |
| 4,753,224 | 6/1988 | Tojo . |
| 4,784,118 | 11/1988 | Fantone et al. . |
| 4,787,370 | 11/1988 | Kanamori . |
| 4,796,604 | 1/1989 | Kawashima . |
| 4,815,833 | 3/1989 | Zobel et al. . |
| 4,838,247 | 6/1989 | Forkner . |
| 4,846,154 | 7/1989 | MacAnally et al. . |
| 4,850,342 | 7/1989 | Hashiguchi et al. . |
| 4,867,529 | 9/1989 | Utsumi et al. . |
| 4,890,905 | 1/1990 | Van Rosmalen et al. . |
| 4,916,534 | 4/1990 | Takahashi et al. . |
| 4,919,112 | 4/1990 | Siegmund . |
| 4,941,457 | 7/1990 | Hasegawa . |
| 4,942,867 | 7/1990 | Takahashi et al. . |
| 4,946,267 | 8/1990 | Hoogland . |
| 4,947,245 | 8/1990 | Ogawa et al. . |
| 4,949,706 | 8/1990 | Thon . |
| 4,964,710 | 10/1990 | Leiner . |
| 4,969,708 | 11/1990 | Leiner . |
| 4,993,817 | 2/1991 | Hoogland . |
| 5,005,960 | 4/1991 | Heimbeck . |
| 5,020,893 | 6/1991 | Karst et al. . |
| 5,046,816 | 9/1991 | Lehmann et al. . |
| 5,059,004 | 10/1991 | Matsumura . |
| 5,142,410 | 8/1992 | Ono et al. . |
| 5,170,454 | 12/1992 | Kanai . |
| 5,184,602 | 2/1993 | Anapliotis et al. . |
| 5,188,092 | 2/1993 | White . |
| 5,188,093 | 2/1993 | Lafferty et al. . |
| 5,190,028 | 3/1993 | Lafferty et al. . |
| 5,193,135 | 3/1993 | Miyagi . |
| 5,199,417 | 4/1993 | Muller et al. . |
| 5,215,077 | 6/1993 | Oku . |
| 5,329,936 | 7/1994 | Lafferty et al. ............................ 128/6 |

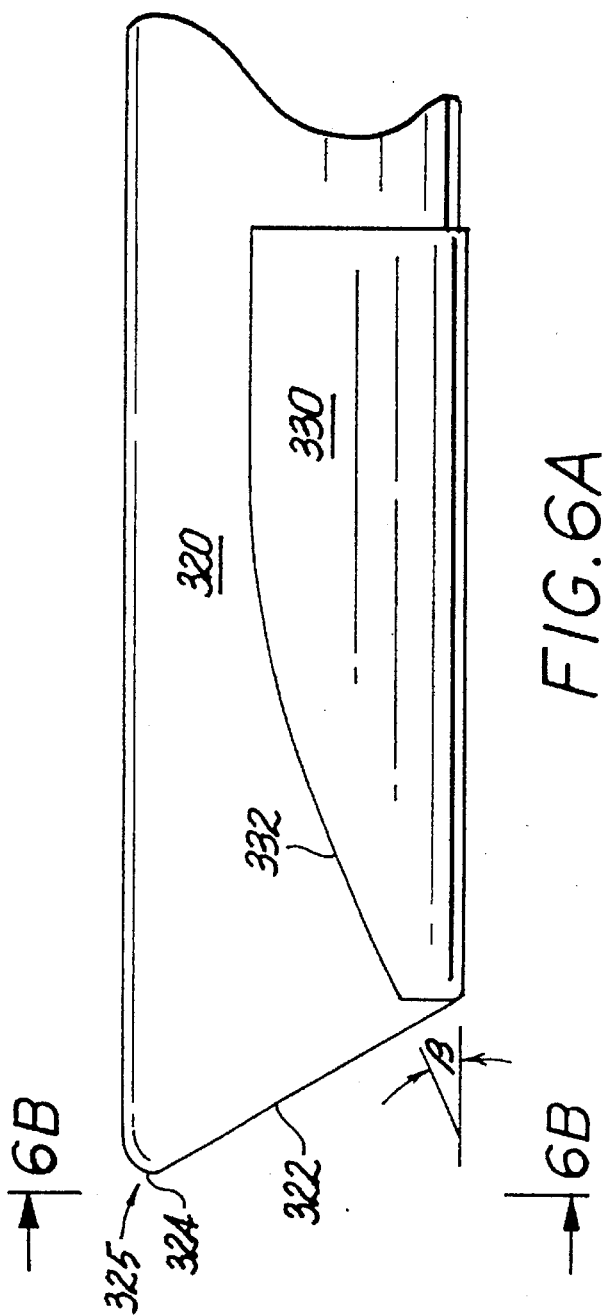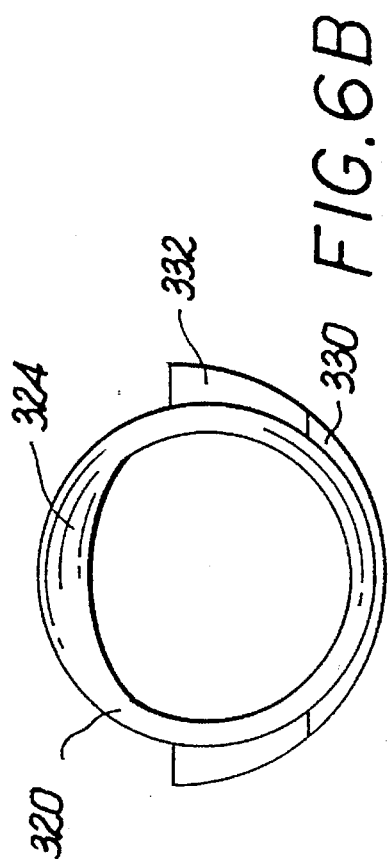

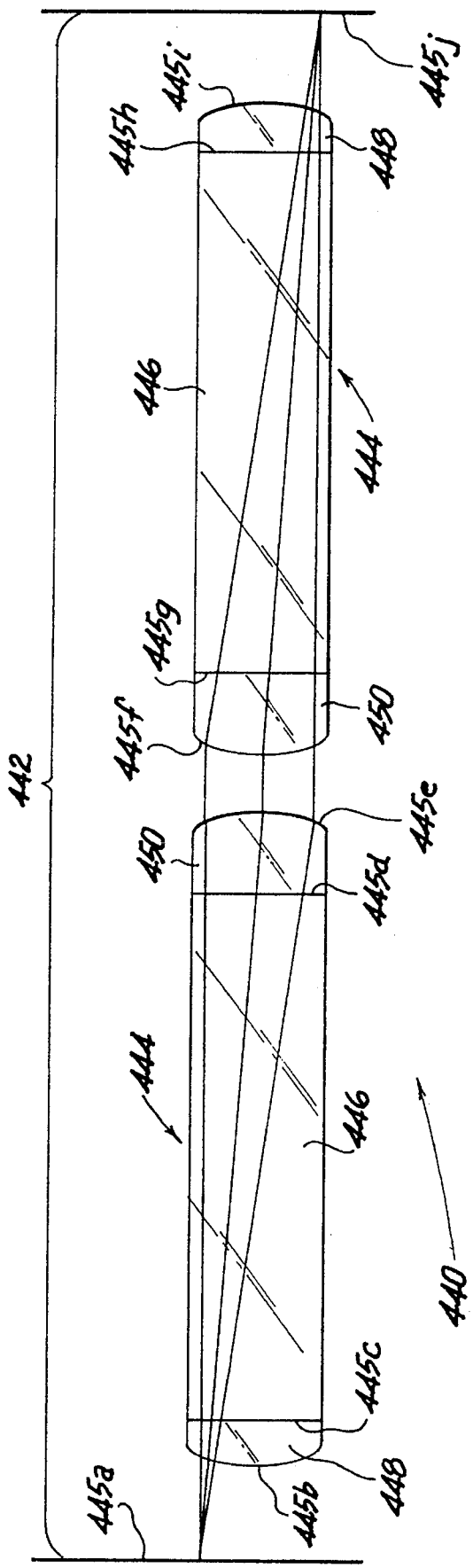
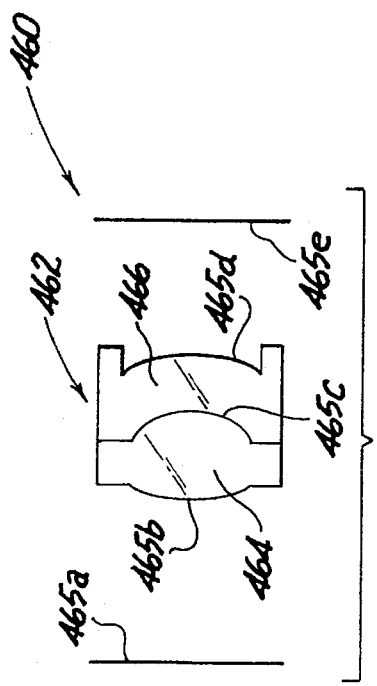
FIG. 15
FIG. 16

ARTHROSCOPE WITH SHIM FOR ANGULARLY ORIENTING ILLUMINATION FIBERS

BACKGROUND OF THE INVENTION

1. Field of the Invention

The present invention relates generally to endoscopic Instrumentation, and, more particularly, to a disposable rigid arthroscope having a direction of view offset relative to the longitudinal axis of the arthroscope.

2. Description of the Prior Art

Endoscopes nave long been used in surgery to view internal portions of a patient's body through a narrow incision in the body exterior or through a naturally occurring hollow viscus. Endoscopes are long, slender instruments having a shaft which is either rigid or flexible, depending upon the procedure being performed. In general, endoscopes include an objective lens positioned adjacent a distal end, and an image transmission system which may include a fiber optic bundle, relay rods or lenses, or a solid state sensor to transmit the image to the viewer. Endoscopes also are usually equipped with an illumination system, such as a fiber optic bundle, which illuminates the area being imaged. Generally, a camera adapter is provided at the proximal end of the endoscope to permit the image to be displayed on a monitor for viewing by the entire surgical team.

Most endoscopes used for medical procedures have a fixed forward viewing angle. Different areas of the body can be imaged by changing the position of the endoscope or, in the case of flexible endoscopes, by bending the distal tip. In these endoscopes, the objective lens is disposed perpendicular to the optical axis of the instrument such that the area directly in front of the instrument is viewed by the user.

Some endoscopes have a direction of view which is offset relative to the optical axis. Examples of endoscopes of this type are disclosed in U.S. Pat. Nos. 4,576,147 to Hashiguchi, 4,615,333 to Taguchi, 4,850,342 to Hashiguchi et al. and 5,184,602 to Anapliotis et al. Such endoscopes, side viewing endoscopes or oblique angle of view endoscopes, make it possible to thoroughly examine interior body spaces, such as the lining of a body cavity, e.g., esophagus, intestinal walls and articular joint spaces, by rotating the instrument. Typically, these side viewing endoscopes incorporate an angle directing prism as part of its objective assembly to redirect the field of view relative to the optical axis. In accordance with the side viewing endoscope, the illuminating fiber optical bundle is typically orientated or bent at an appropriate angle at its light emitting distal end to direct light onto the field of view.

One type of endoscope which may incorporate inclined angle of view capability is an arthroscope. Arthroscopes are used to examine the interior structure of a body joint, for example, a knee, in order to determine the extent of damage to the joint. Arthroscopes are typically smaller in diameter than other types of endoscopes, such as laparoscopes, to enable the scope to fit into the relatively small joints of the bone, particularly the wrist and foot. Examples of arthroscopes are disclosed in U.S. Pat. Nos. 4,838,247 to Forkner, 5,188,093 to Lafferty et al. and 5,190,028 to Lafferty et al.

Known endoscopes and arthroscopes having an inclined direction of view such as the scopes disclosed in the aforementioned patents have their own particular shortcomings. For example, the construction of such endoscopes is typically costly, thereby precluding the economic feasibility that such scopes may be disposed after a single use. Furthermore, properly positioning and retaining the illuminating optical fibers in a manner such that the light emitting end portions of the fibers 0 directly illuminate light in the perspective visual field direction often entails substantial modification to the endoscopic tube and/or the incorporation of adapters and/or attachments within the distal end of the scope.

U.S. Pat. No. 4,576,147 to Hashiguchi describes an endoscope with an inclined angle of view wherein a tip member, positioned within each of a lens carrying inner tube and an outer tube, and a saddle shaped pressing member, soldered to the tip member of the inner tube, cooperate to orientate the optical fiber end portions in the visual field direction. A disadvantage of the Hashiguchi '147 endoscope is that the additional components e.g., the tip members within each of the inner and outer tubes and the pressing member, need to be precisely manufactured in order to be incorporated within the endoscope, thus increasing the cost of the endoscope. Furthermore, such components require additional steps in the assembly of the Hashiguchi '747 endoscope, further increasing the cost of manufacture of the scope.

A further disadvantage with the construction of known endoscopes of the type having inclined angles of view concerns mounting the distal optical components within the distal end of the endoscope. For example, the endoscope described in U.S. Pat. No. 4,850,342 to Hashiguchi et al. incorporates several frame members which are fitted within the lens carrying inner tube to mount the objective prism and the objective lens components within the tube. The distal most cover glass of the Hashiguchi '342 endoscope is mounted via a housing member and a separate fastening ring which is fitted within an opening in the housing member.

Accordingly, it would be desirous to provide a disposable endoscope, particularly an arthroscope, having 0 an inclined angle of view that can be manufactured and assembled efficiently. It would be further desirous for such arthroscope to direct illuminating light in the field of view without requiring extensive modification to the endoscopic tube member or the incorporation of high precision fitting members and adapters. It would also be advantageous for the arthroscope to incorporate features to positively mount the objective lens elements within the distal end of the scope without requiring additional lens mounting components.

SUMMARY OF THE INVENTION

Generally stated, the present invention is directed to a disposable rigid arthroscope having an inclined angle of view. The arthroscope comprises a frame member, an outer tube member extending distally from the frame member, an inner lens tube member eccentrically disposed within the outer tube member, optical means disposed within the inner lens tube member and having means for altering the field of view with respect to the optical axis and an illumination system including a plurality of optical fibers. The optical fibers of the illumination system are assembled and oriented to emit light in the general direction of the inclined field of view so as to sufficiently illuminate the surgical field. The materials of the arthroscope are advantageously selected to minimize the overall cost of the scope while providing for high level optical performance.

Further features of the invention, its nature and various advantages will be more apparent from the accompanying drawings and the following detailed description of the invention.

BRIEF DESCRIPTION OF THE DRAWINGS

Preferred embodiments of the invention are described hereinbelow with reference to the drawings wherein:

FIG. 6A is a side plan view of the distal end of the inner lens tube with an optical fiber orientating shim member positioned thereabout;

FIG. 6B is a distal end view of the inner lens tube and shim;

FIG. 15 is an optical schematic view of the relay lens assembly of the arthroscope of FIG. 1 illustrating ray path and image orientation; and FIG. 16 is an optical schematic view of the eye lens assembly of the arthroscope of FIG. 1.

DETAILED DESCRIPTION OF THE PREFERRED EMBODIMENTS

Figure 1:
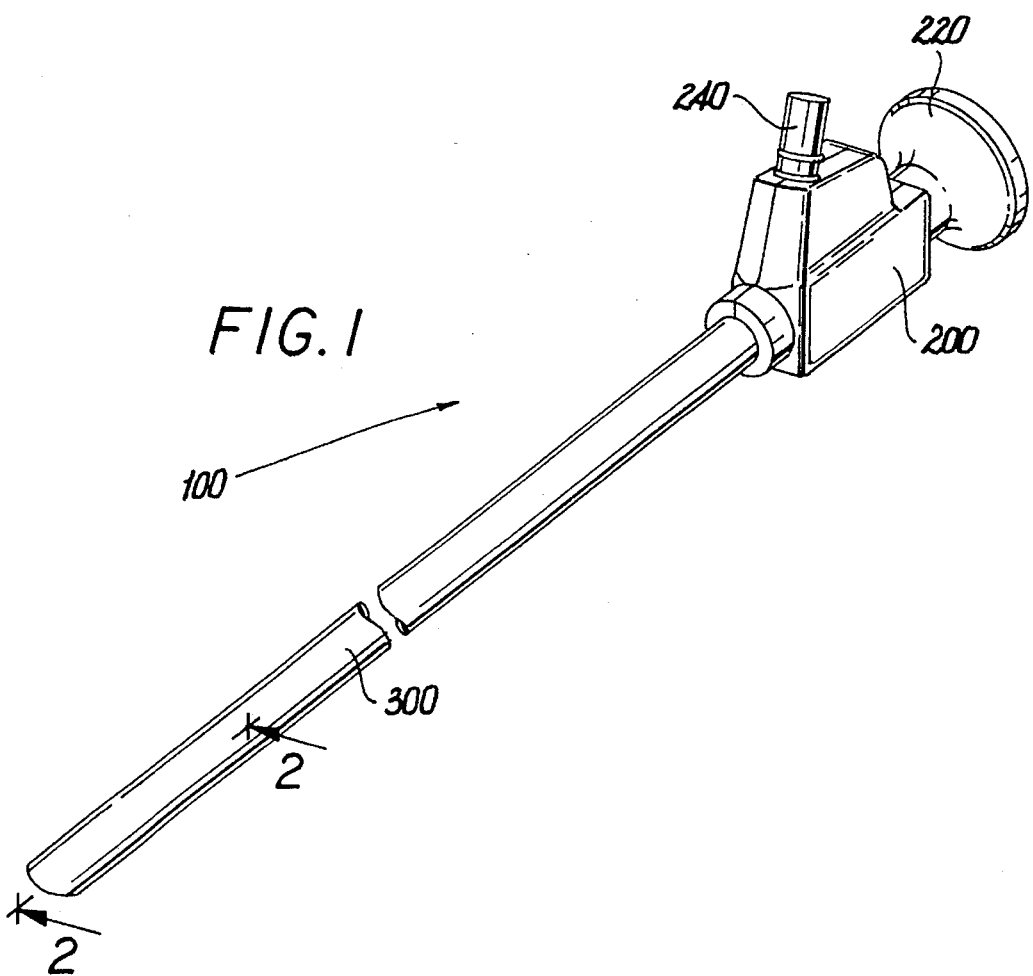
FIG. 1 is perspective view of the disposable arthroscope constructed according to the principles of the present invention.

Referring now to the drawings, in which like reference numerals identify similar or identical elements throughout the several views, FIG. 1 illustrates, in perspective view, an arthroscope 100 having an inclined angle of view constructed according to the principles of the present invention. Arthroscope 100 includes housing portion 200 and endoscopic portion 300 extending distally from the housing portion 200. Housing portion 200 supports eye piece assembly 220 which contains the eye lens assembly for viewing the image of the object formed by the optical system of the arthroscope, and light guide connector 240. Light guide connector 240 connects a light guide (not shown) which provides illuminating light to the illumination system of arthroscope 100. The components and function of light guide connector 240 will be discussed in greater detail below.

Figure 2:
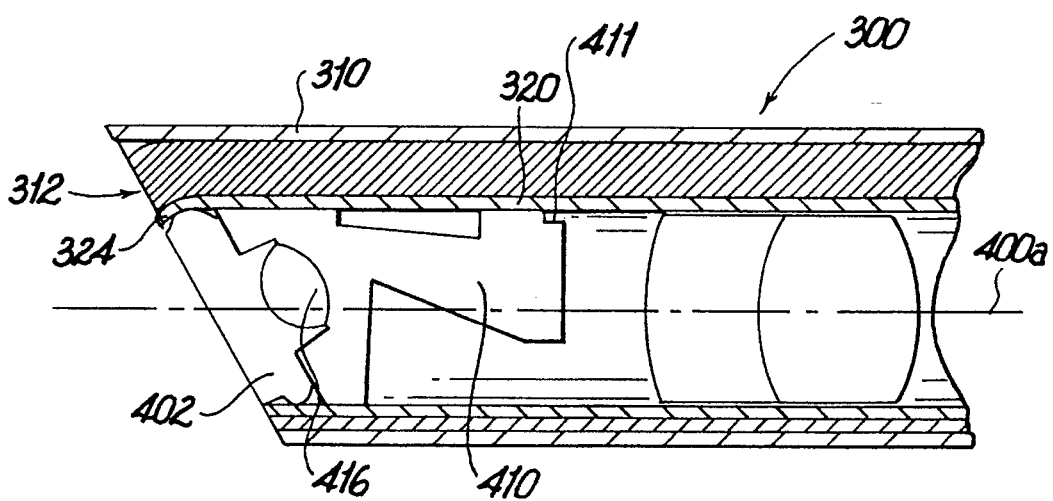
FIG. 2 is an enlarged cross-sectional view taken along the lines 2—2 of FIG. 1 illustrating the inner lens tube of the arthroscope mounted within the outer tube.
Figure 9:
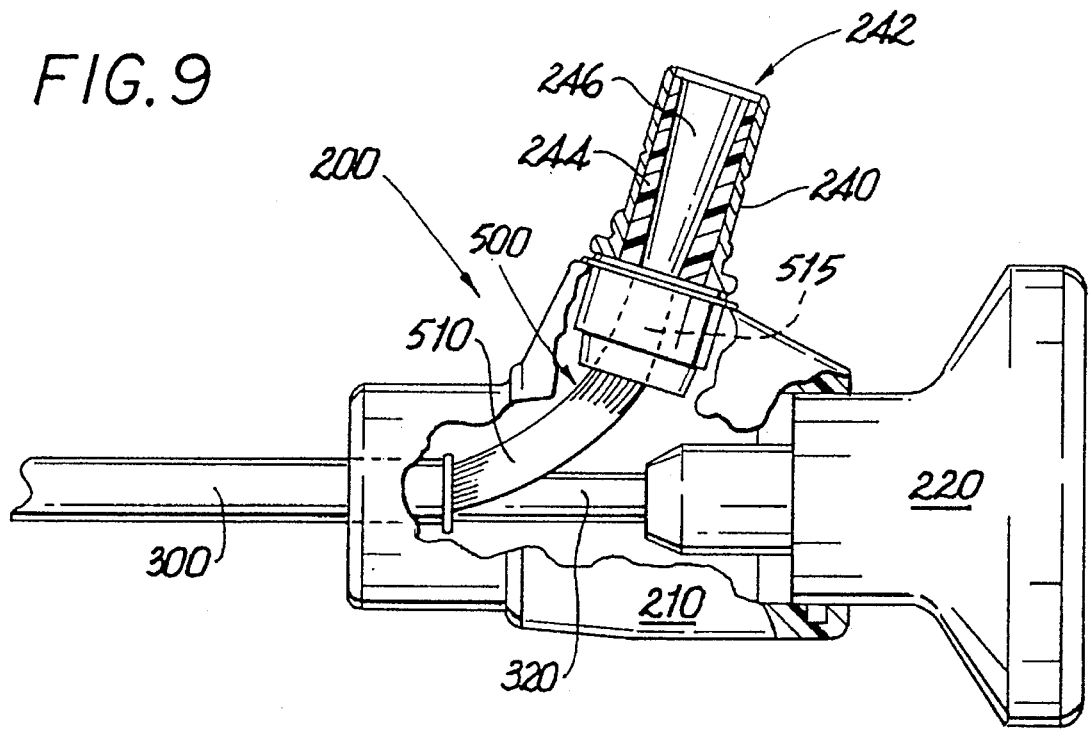
FIG. 9 is a side plan view in partial cross-section of the housing portion of the arthroscope illustrating the light guide connector with an illuminating coupler positioned therein.

Referring now to FIG. 2, in conjunction with FIG. 1, endoscopic portion 300 of arthroscope 100 will be discussed in detail. Endoscopic portion 300 includes outer tube 310 and inner lens tube 320 disposed eccentrically within the outer tube 310. Outer tube 310 is preferably fabricated from a rigid material such as stainless steel or the like. Inner lens tube 320 is also preferably fabricated from stainless steel and houses the optical components of the objective and relay lens systems of the optical system. Inner lens tube 320 extends along the entire length of outer tube 310 and terminates within housing portion 200 at a position adjacent the eye lens assembly as shown in FIG. 9.

Referring again to FIGS. 1 and 2, distal end surface 312 of outer tube 310 is oblique or inclined, i.e., angularly offset relative to a plane extending generally transversely to the axis of endoscopic portion 300. In the preferred 30° arthroscope, the distal end surface 312 defines an angle of about 30° relative to the transverse plane. Similarly, distal end surface 322 of inner lens tube 320 is inclined at an angle "Θ" (FIG. 3A) which measures about 30°. Although a 30° angle is preferred, the present invention is not so limited and could be within a range from 0°<Θ<135°.

Figure 3A:
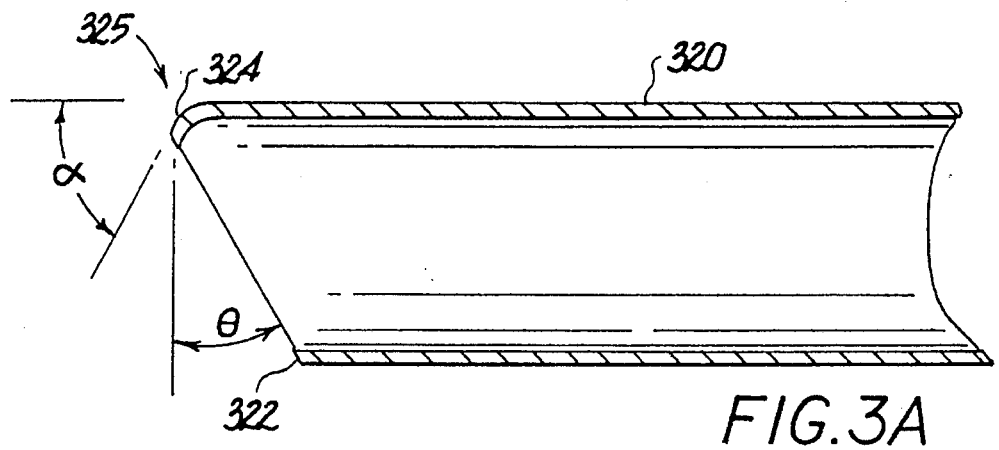
FIG. 3A is a cross-sectional view of the distal end of the inner lens tube of the arthroscope.
Figure 3B:
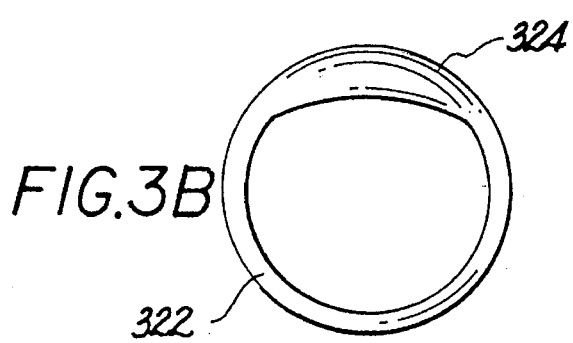
FIG. 3B is a transverse cross-sectional view of the inner lens tube of the arthroscope.

Referring now to FIGS. 2 and 3A–3B, distal end surface 322 of inner lens tube 320 includes a curved lip portion 324 at an upper portion of the lens tube. Lip portion 324 functions in mounting the distal optical components within inner lens tube 320 and also in positioning the optical fibers of the illumination system as will be discussed in greater detail below.

Lip portion 324 is preferably formed by initially curling the distal end surface of a cylindrical tube inwardly and thereafter cutting the distal end at the prescribed angle, i.e., 30° to provide the oblique distal end surface 322 with the lip portion 324 on a portion of the extreme distal tip portion of the tube. Preferably, the outer surface 325 of lip portion 324 defines an angle "α" (FIG. 3A) of about 60° with respect to the longitudinal axis of inner lens tube 320 to concentrate illuminating light within the offset field of view.

Figure 4A:
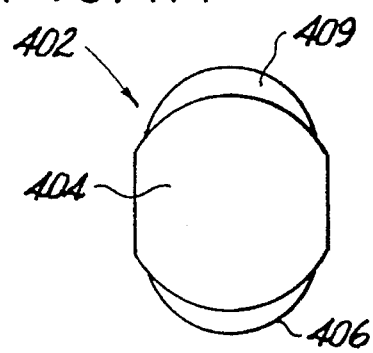
FIG. 4A is a distal end view of the distal cover lens of the arthroscope.
Figure 4B:
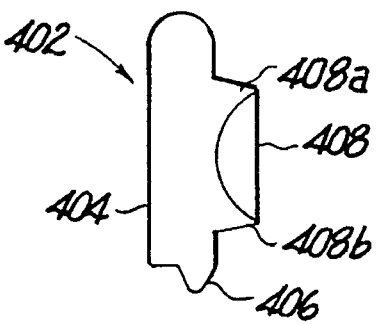
FIG. 4B is a side plan view of the distal cover lens of the arthroscope.

Referring now to FIGS. 2, 4A–4B and 5A–5B, the novel method for positively mounting the distal lens components of the optical system 400 within inner lens tube 320 will be discussed in detail. FIGS. 4A–4B illustrate the distal most cover lens element 402 of the optical system. Cover lens 402 encapsulates the optical components within lens tube 320 as shown in FIG. 2 and has a distal face 404 which, when mounted within inner lens tube 320, is angled at 30° relative to optical axis 400a of the optical system 400. Cover lens 402 also has a lower edge 406 which defines a generally arcuate cross-section and conforms to the shape of inner lens tube opposite lip portion 324 when the top of cover lens 402 is disposed against lip portion 324. The proximal face 408 of cover lens 402 includes two projecting portions 408a, 408b, which mate to prism 410.

Prism 410 redirects the field of view relative to the optical axis "400a" (FIG. 2) of optical system 400. Prism 410 includes lower and upper arcuate surfaces 412, 414 (FIG. 5A) which generally conform to the shape of inner lens tube 320 and a recessed or notched portion 411 at its proximal end to accommodate glue or adhesives which are used in mounting the prism within lens tube 320 and to an adjacent optical component. The optical characteristics of prism 410 will be discussed in greater detail below.

During assembly, projections 408a, 408b are positioned within recess 416 of prism 410 in the manner depicted in FIG. 2. Thereafter, projections 408a, 408b are adhered to prism 410 by adhesives, cements or the like to form a one-piece assembled unit. Cover lens 402 and adhered prism 410 are then inserted into the proximal end of lens tube 320 and advanced into the lens tube until distal face 404 of cover lens 402 contacts lip portion 324 of the lens tube 320. Distal cover lens 402 and prism 410 are positively constrained within inner lens tube 320 due to the engagement of edge 406 of cover lens 402 with the lower surface of the lens tube 320 and the engagement of upper edge 409 of cover lens 402 with curved lip portion 324 of the lens tube 320. Furthermore, cover lens 402 and prism 410 are prevented from tipping proximally and/or distally due to the engagement of lower and upper surfaces 412, 414 (FIG. 5A) of prism 410 with the interior of inner lens tube 320. Similarly, cover lens 402 and prism 410 are prevented from rotating due to the constraining action of curved lip portion 324. The remaining optical components of the optical system, including the objective and relay lens assemblies, are mounted within inner tube 320 by insertion of each component in the proximal end of the inner tube and mounting these components in a conventional manner.

Figure 7A:
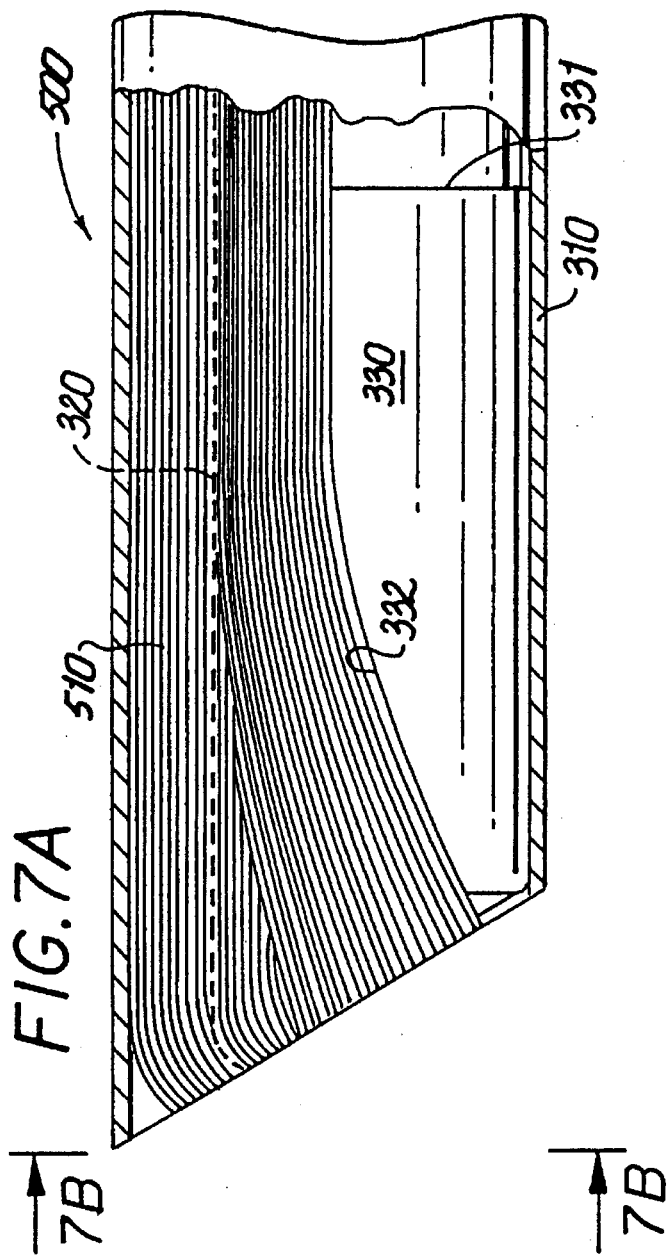
FIG. 7A is a side plan view of the distal end of the arthroscope with portions of the outer tube cut away illustrating the orientation of the illuminating optical fibers about the inner lens tube and the shim.
Figure 7B:
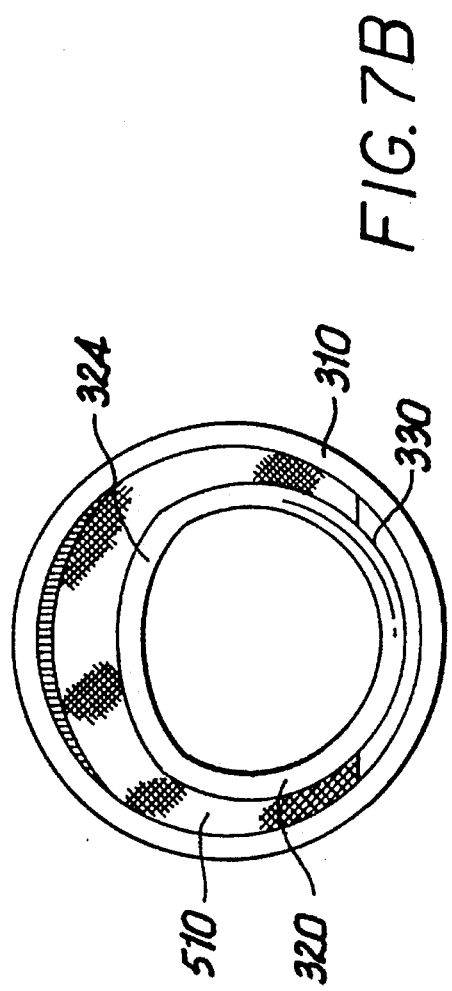
FIG. 7B is a distal end view of the arthroscope further depicting the orientation of the optical fibers.

Referring now to FIGS. 6A–6B and 7A–7B, the novel mechanism for orientating the optical fibers of the illumination system 500 to direct illuminating light in the perspective visual field as provided by prism 410 will be discussed in detail. An optical fiber orientating shim 330 is positioned about the lower peripheral surface of inner lens tube 320. Shim 330 serves as a guide to position the end portions of each illumination fiber 510 at a desired orientation so as to direct light emitted by the optical fibers into the field of view of the arthroscope. Shim 330 includes two side portions 332 which are sloped downwardly towards the lower portion of inner lens tube 320. In the preferred 30° arthroscope, each side portion 332 defines an angle "β" (FIG. 6A) of about 30° relative to the optical axis such that the illumination fiber end portions 510, disposed on either side of lens tube 320, are oriented at a 30° angle relative to optical axis 400a (FIG. 2), and perpendicular to distal end surface 322 of the inner lens tube 320. The remaining illumination fiber end portions 510 disposed adjacent the top of the inner lens tube 320 are oriented to direct light in the field of view by the angled peripheral surface 325 of curved lip portion 324 at distal end face 322. Thus, sloped side portions 332 of shim 330 in combination with the peripheral surface 325 of curved lip portion 324 effectively position and retain the end portions of illumination fibers 510 at the desired 30° orientation in the assembled condition of arthroscope 100. As best shown in FIG. 7B, illumination fibers 510 are disposed in a crescent-shaped array about inner lens tube 320 within the space defined by outer lens tube 310, inner lens tube 320 and shim 330 when assembled within arthroscope 100. Preferably, the fibers 510 are placed onto the inner lens tube 320 about shim 330 and within the outer tube 310 prior to assembly of the optical assembly within the inner tube.

Shim 330 is preferably formed by replica molding techniques. In the preferred method, a Teflon mold (not shown) made in the shape of the shim 330 is provided. The mold has sides angled at the desired curvature of side portions 332 of shim 330. To form shim 330 directly onto inner lens tube 320, a drop of ultraviolet (UV) curing cement is placed at the bottom of the mold. Inner lens tube 320 is then oriented in the mold (related positioning fixtures may be used), causing the uncured cement to surround inner lens tube 320 in the shape of the mold. A UV light is then activated to cure the cement. Inner lens tube 320 can then be removed from the mold with shim 330 formed thereon. Replica molding techniques are desirable for forming shim 330 on inner lens tube 320 in that such techniques are capable of forming precision shim components relatively inexpensively and in large quantities. Further, such molding technique positively fixes shim 330 to inner lens tube 320, thus, eliminating an assembly step which would otherwise be necessary during manufacture of arthroscope 100.

Shim 330 also assists in positively positioning inner lens tube 320 within outer tube 310. As shown in FIGS. 2 and 7A–7B, the proximal end portion 331 of shim 330 preferably extends to the maximum inner diameter of outer tube 310 (e.g., defines a major cross-sectional dimension or diameter which approximates the major inner dimension or inner diameter of the outer tube 310) and fills the space surrounding the lower portion of inner lens tube 320. Thus, inner lens tube 320 is prevented from side to side movement within outer tube 310 and up and down movement within the outer tube by the engagement of shim 330 with the inner walls of the outer tube.

In the preferred method for positioning illumination fibers 510 of illumination system 500 about shim and within arthroscope 100, the illumination fibers 510 are placed into outer tube 310. Inner lens tube 320, already cut at an angle and having curved lip portion 324 formed thereon, is inserted into outer tube 310 with the fibers 510 disposed within the space defined between the two tubes. At this point in the procedure, the fibers extend out of both ends of outer tube 310. A collar may be placed around illumination fibers 510 at the proximal end of outer tube 310 and the collar positioned within a jig. The jig positions the collar, fibers 510 and tube 310 in the orientation they will assume in the final assembled condition of arthroscope 100. A heat curing cement is placed around the fibers at the collar and the entire device is heated to bond the fibers within and to the collar. A heat curing cement is acceptable where glass fibers ere used. If desired, particularly if plastic fibers are used, a UV curing cement may be utilized.

At the distal end of outer tube 310, illumination fibers 510 are divided into a middle (top) group and two side groups. Each group is bent downwardly. The top group of fibers 510 is guided at the appropriate angle by curved lip portion 324 of inner lens tube 320. The side groups of fibers are guided by shim 330. All groups are restrained in their respective positions by a fixture. Cement (which may again be heat cured) is applied to the three groups of fibers 510 and cured.

In the preferred method, cementing of the fibers at the distal end is a two-step process. A low viscosity cement is first applied and is wicked along fibers 510 inside inner tube 320. Suitable cements for this purpose are manufactured by Epoxy Technology of Watertown, Mass., under the tradenames EPO TEK 350ND and EPO TEK 350ND-T. The first cement is baked to cure and a second, high viscosity cement is applied to fill any voids around fibers 510 at the distal end surface 322 and to act as a sealant to prevent moisture and/or bodily fluids from contacting the lenses of the optical system. A suitable high viscosity cement is Vitralit 1710 manufactured by Elosol Ltd. of Zürich, Switzerland. The second cement is baked to cure. The excess ends of fibers 510 are cut, and the fiber surfaces at the proximal and distal ends are ground and polished. If necessary, it is contemplated a sealant could be applied to the distal end of the scope. The aforementioned Vitralit 1710 is appropriate for use as a sealant for this purpose. Once inner tube 320 is fully assembled within outer tube 310, fibers 310 are compressed and retained at their appropriate angular orientation by side edges 332 of shim 330 and surface 325 of inner lens tube 320.

Figure 8A:
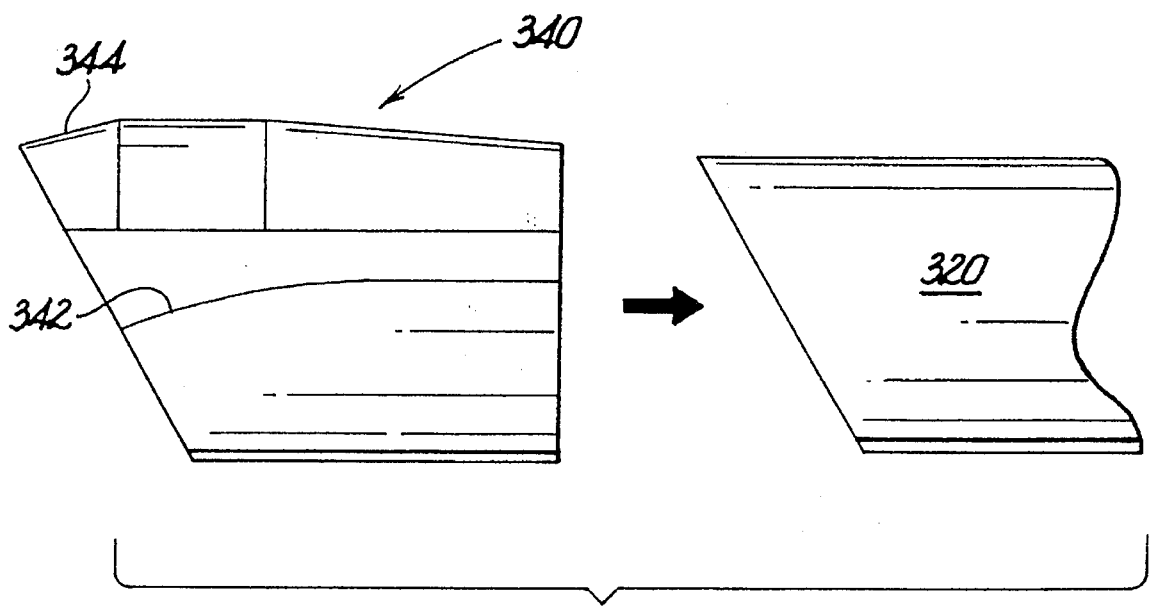
FIG. 8A is a side plan view of an alternative optical fiber orientating shim and the distal lens of the inner tube depicting the shim prior to positioning about the lens tube.
Figure 8B:
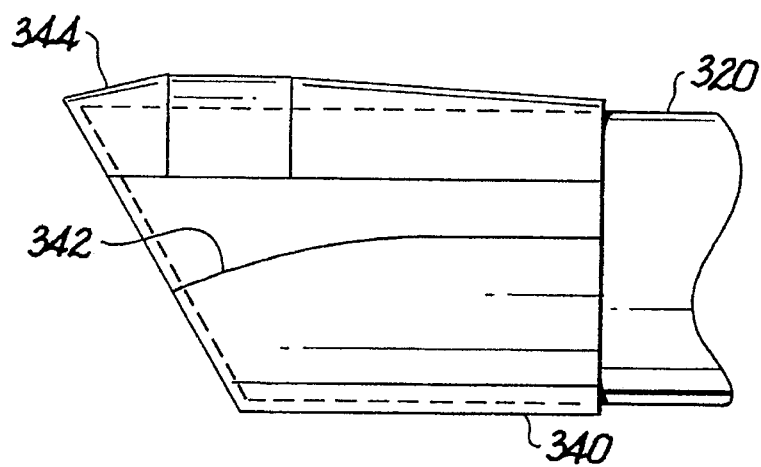
FIG. 8B is a side plan view of the alternative shim positioned about the entire periphery of the inner lens tube.
Figure 8C:
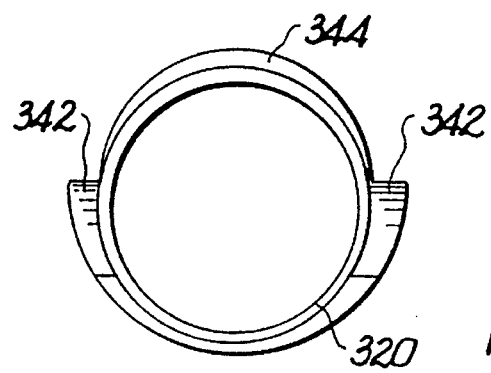
FIG. 8C is an distal end view of the inner lens tube and alternative shim.

Referring now to FIGS. 8A–8C, an alternative embodiment of the fiber orienting shim is illustrated. In this embodiment, shim 340 extends about the entire periphery of the distal end of inner lens tube 320. Shim 340 includes side portions 342 which are sloped downwardly at an angle relative to the axis of inner lens tube 320 in a similar manner to that described in connection with the previous shim. Upper distal surface 344 of shim 340 is also sloped downwardly. Side portions 342 and sloped upper surface 344 position optical fibers 510 in a manner substantially similar to that described in connection with the shim of FIGS. 6A and 6B. In particular, the top group of fibers 510 adjacent the upper portion of outer tube 310 are guided by the angled surface of distal surface 344 of shim 340 and the side groups of fibers are positioned by side portions 342. Thus, in accordance with this embodiment of shim 340, it is not necessary to form the curved lip portion 324 of inner lens tube 320 to guide the top group of fibers. Shim 340 may be formed by conventional molding techniques or, in the alternative, by a replica molding technique. Optical fibers 510 are disposed in a similar crescent shaped array as the embodiment illustrated in FIG. 7B.

Optical fibers 510 of illumination system 500 are each preferably glass fibers having a diameter which enables the fibers to be bent and oriented about shim 330, 340. In the preferred embodiment, fibers 510 may have a diameter ranging from about 50 microns to about 90 microns.

Referring now to FIG. 9, in conjunction with FIG. 1, housing portion 200 of arthroscope 100 includes two housing half sections 210. Half sections 210 are preferably formed of a suitable plastic material such as ABS (acrylonitrile butadiene styrene), polycarbonate, polypropylene, polyethylene or the like, or, in the alternative, of a metal such as stainless steel, and are attached along a seam by suitable attachment techniques, including adhesives and/or ultrasonic welding. Eye piece assembly 220 is secured within the proximal end of housing 200 by conventional means.

Figure 10:
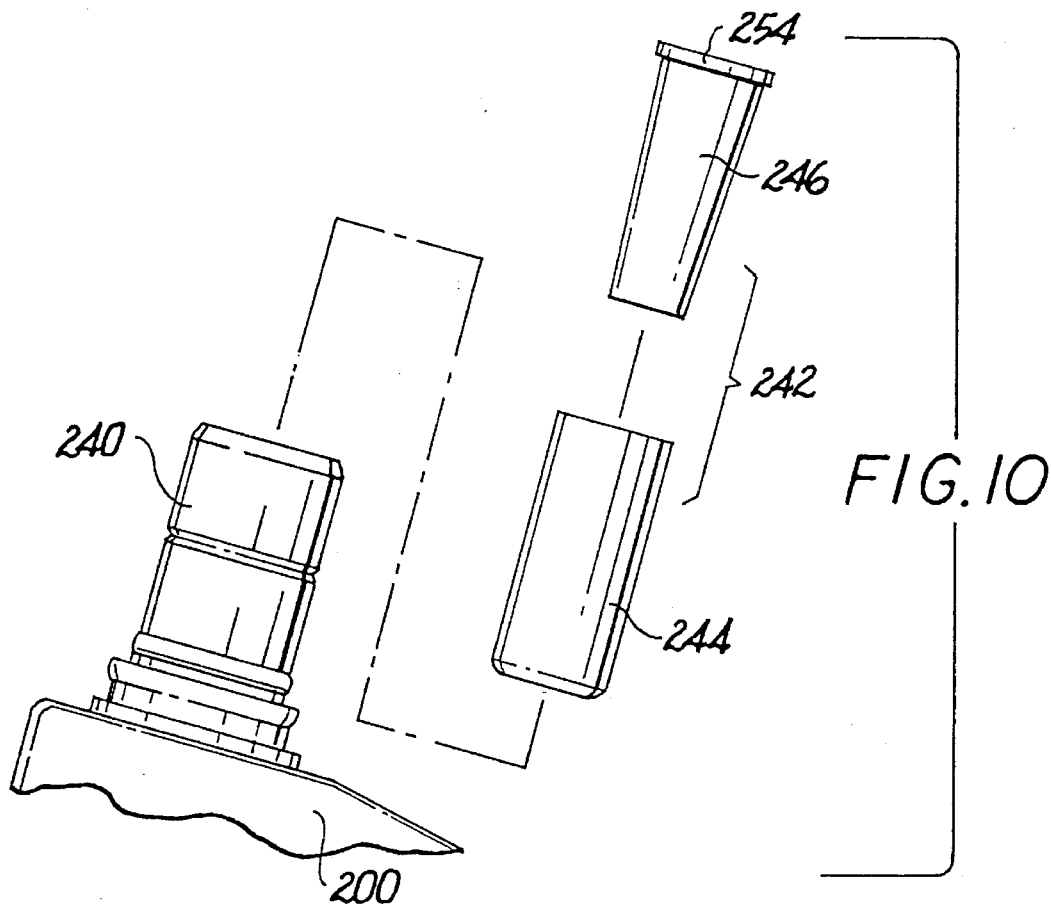
FIG. 10 is a plan view with parts separated of the light guide connector and illuminating coupler illustrating the support member and the light transmissive element of the illuminating coupler.
Figure 11A:
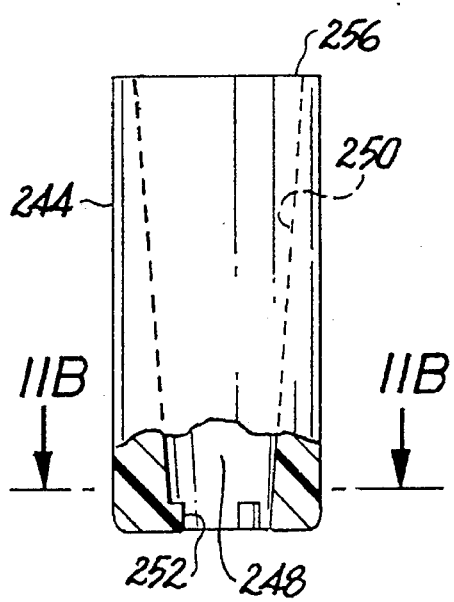
FIG. 11A is a side plan view in partial cross-section of the coupler support member of the illuminating coupler of FIG. 10.
Figure 11B:
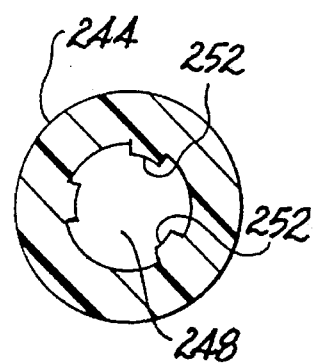
FIG. 11B is an axial view of the coupler support member of FIG. 11A.

Referring now to FIGS. 1, 9, and 10, the novel mechanism for coupling light into the illumination system of arthroscope 100 will be discussed in detail. By way of background, conventional light guides connected to a light source typically have a working diameter or illuminating aperture of about 5 mm to correspond to conventional endoscopes which also typically have a 5 mm diameter entrance or illuminating aperture as defined by the entrance end of the fiber optic bundle of the illumination system. However, since arthroscopes, including arthroscope 100 of the present invention, are typically smaller in diameter than conventional endoscopes, the entrance illuminating apertures of such arthroscopes are also smaller. In particular, the entrance illuminating aperture of arthroscope 100 of the present invention, as defined by the proximal entrance end 515 of fiber optic bundle 500 (See FIG. 9) ranges from about 2–2.5 mm. In order to minimize loss of light from a 5 mm light guide, an illuminating coupler 242 is provided.

Figure 13:
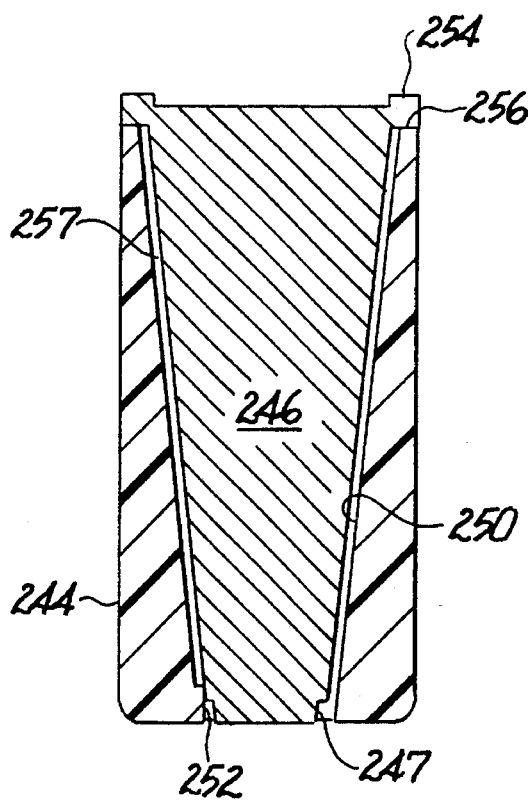
FIG. 13 is a cross sectional view of the illuminating coupler of FIG. 10 illustrating the light transmissive element mounted within the support member.
Figure 12:
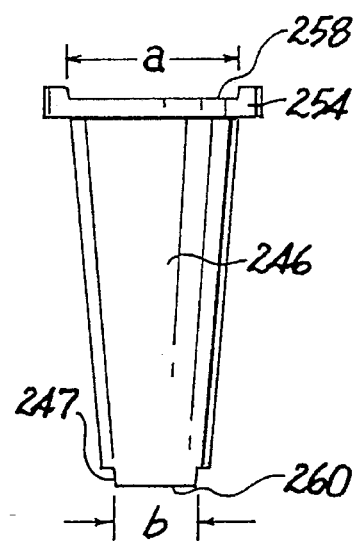
FIG. 12 is a side plan view of the light transmissive element of the illuminating coupler of FIG. 10.

Referring now to FIGS. 9–13, illuminating coupler 242 is disposed within light guide connector 240 and includes support member 244 and a light transmissive optical element 246 disposed within the support member. Support member 244 is generally cylindrically shaped and includes a generally frustoconical inner chamber 248 as defined by the tapering inner walls 250 of the support member 244. The lower portion of support member 244 includes three projections 252 which extend into chamber 248. Light transmissive element 246 is generally frustoconically shaped and includes a circumferential ledge 254 at its larger diameter portion and a peripheral recessed portion or well 247 at its lower end portion. In the assembled condition of frustoconical optical element 246 within support member 244 as shown in FIGS. 9 and 13, the frustoconical element 246 is spaced from the support member 244 by an air gap. Such spacing is provided by the engagement of projections 252 with the lower end portion of frustoconical element 246. Also, in the assembled condition, circumferential ledge 254 of frustoconical element 246 rests on the upper surface 256 of support 244 to assist in mounting the frustoconical element 246 within the support 244. The lower surface 260 of frustoconical element 246 and optical fibers 510 at proximal entrance end 515 are disposed in face-to-face relation as best shown in FIG. 9. Preferably, an epoxy glue is applied between lower surface 260 and the proximal entrance end 515 to maximize coupling efficiency between the fibers 510 and the lower surface 260. Recessed portion 247 of frustoconical element 246 accommodates any excess epoxy glue which may overflow into this area so as to ensure that a bead does not form at the lower end portion of the frustoconical element 246. The formation of an epoxy bead would degrade the light transmissive characteristics of frustoconical element 246.

Illuminating coupler 242 minimizes the loss of light when a light guide having a relatively large working diameter, typically 5 mm, is coupled to light guide connector 240 of arthroscope 100 which possesses an illumination aperture of about 2.5 mm. In particular, light entry side 258 of frustoconical element 246 has a working diameter "a" (FIG. 12) of about 5 mm. The smaller diameter exit side 260 of element 246 which is adjacent the proximal end 515 of the illumination system has a diameter "b" of about 2.5 mm. Accordingly, light expelled from a 5 mm light guide onto entry side 258 of light transmissive element 246 is directed through the frustoconical element 246 and released from the 2.5 mm diameter exit side 260 of the element onto the proximal end of the optical bundle. Due to the differences in the indices of refraction of frustoconical element 246 (nd of about 1.5) and air (nd=1.0), the air gap defined between frustoconical element 246 and support 244 minimizes leakage of light from element 246 thereby ensuring maximum transfer of illuminating light through element 246 and into illumination system 500.

Light transmissive element 246 is preferably molded of acrylic or polycarbonate. The inner walls 250 of support member 244 may be ground from a 0.25 microfinish to about a 0.45 microfinish, which produces a highly reflective surface to direct any stray light back into light transmissive element 246. The walls of light transmissive element 246 may also be cladded with a reflective aluminum coating, which would obviate the need to suspend the cone in air.

Figure 14:
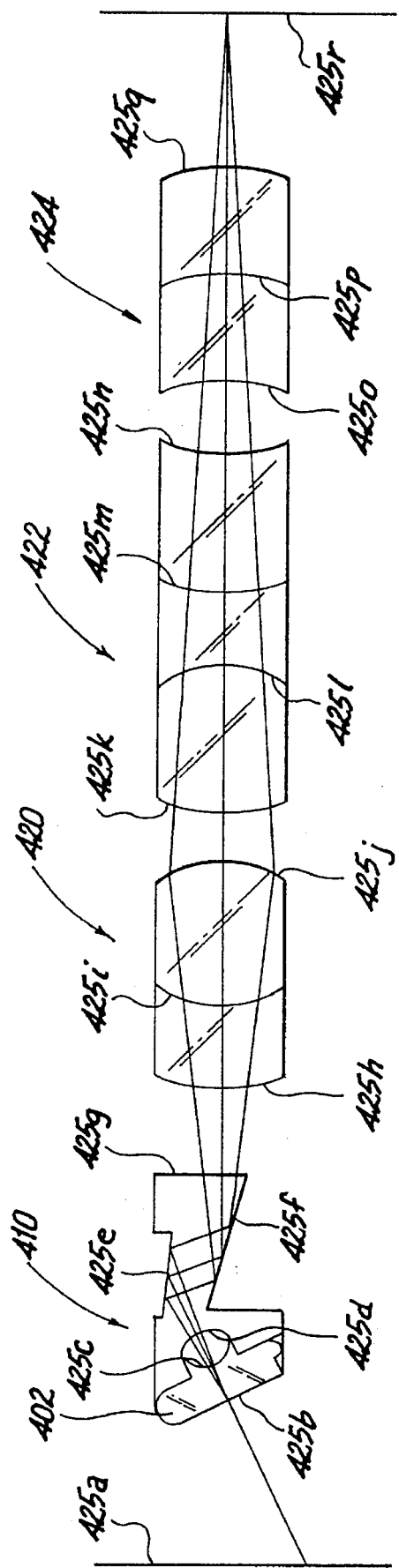
FIG. 14 is an optical schematic view of the objective lens assembly of the arthroscope of FIG. 1 illustrating ray path and image orientation.

Referring now to FIGS. 14–16, the optical system of the present invention is illustrated in detail. The optical system includes an objective lens assembly (FIG. 14) for forming an image of an object, a relay lens assembly 440 (FIG. 15) for transferring the image through endoscopic portion 300 and eye lens assembly 460 (FIG. 16) for viewing the transferred image.

As shown in FIG. 14, objective lens assembly includes distal cover lens 402, prism 410, first or distal doublet 420, triplet 422 and second or proximal doublet 424. An aperture stop may be provided between prism 410 and first doublet 420 to limit the diameter of the light rays transferred through the system. Cover lens 402 is a plano concave lens. Prism 410 is preferably molded of a suitable polymeric material including styrene, polycarbonate and acrylic or, in the alternative, may be formed from an optical glass. The prism may also be formed of molded glass.

Figure 5A:
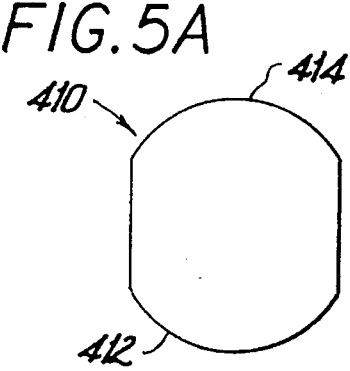
FIG. 5A is a distal end view of the prism for altering the angle of view of the arthroscope.
Figure 5B:
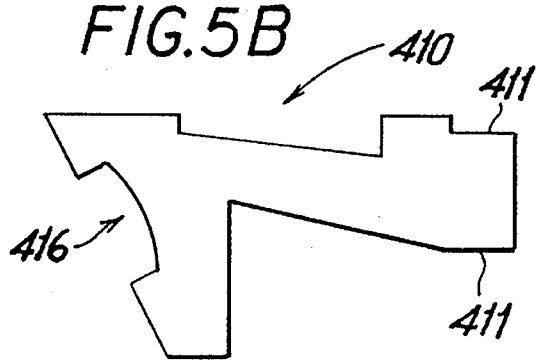
FIG. 5B is a side plan view of the prism.

Referring to FIGS. 5A–5B and 14, prism 410 is a 30° deflection prism which changes the direction of view of arthroscope 100 from forward viewing to viewing at an oblique angle, i.e., at a 30° angle relative to the optical axis of the optical assembly. In a preferred embodiment, prism 410 is a hybrid prism, i.e., one which principally reflects light, but, also refracts the light so as to change the angle of view. In the alternative and depending on the particular applications, prism 410 may be a full reflection prism or a full refraction prism. A full refraction prism is preferably used when it is desirable to change the angle of view less than 30° relative to the optical axis. Other suitable methods for altering the angle of view, such as mirrors and fiber optics, may also be utilized.

FIG. 14 illustrates ray path and image orientation through the objective lens assembly. The geometrical characteristics of the objective assembly are defined by an object plane 425a, surfaces 425b–c of cover lens 402, surfaces 425d–g of prism 410, surfaces 425h–425j of first doublet 420, surfaces 425k–425n of triplet 422, surfaces 425o–425q of doublet 424 and exit image plane 425r, respectively. The geometrical and optical parameters of the objective assembly are recorded in Table 1 below. In the Table, surfaces A, B–C, D–G, H–J, K–N, O–Q and R correspond to object plane 425a, surfaces 425b–c of cover lens 402, surfaces 425d–g of prism 410, surfaces 425h–425j of first doublet 420, surfaces 425k–425n of triplet 422, surfaces 425o–425q of second doublet 424 and exit image plane 425r, respectively.

TABLE 1

| SURFACE | RADIUS | THICK-NESS | MEDIUM | INDEX | ABBE NO. |
|---|---|---|---|---|---|
| A | Object Plane | (Object Distance) | AIR | 1.000 | |
| B | Plano | 0.7 | Styrene | 1.590 | 30.9 |
| C | 0.800 | 0.7 | AIR | 1.000 | |
| D | −1.100 | 1.0 | Styrene | 1.590 | 30.9 |
| E | Plano | 1.4 | Styrene | 1.590 | 30.9 |
| F | Plano | 1.4 | Styrene | 1.590 | 30.9 |
| G | Plano | 0.2 | AIR | 1.000 | |
| H | 19.763 | 1.0 | Styrene | 1.590 | 30.9 |
| I | 1.500 | 1.9 | Acrylic | 1.492 | 57.4 |
| J | −2.062 | 0.3 | Air | 1.000 | |
| K | 4.132 | 2.5 | Acrylic | 1.492 | 57.4 |
| L | −1.500 | 1.0 | Styrene | 1.590 | 30.9 |
| M | 4.000 | 1.4 | Acrylic | 1.492 | 57.4 |
| N | 2.304 | 0.6 | AIR | 1.000 | |
| O | 2.391 | 2.0 | Acrylic | 1.492 | 57.4 |
| P | −4.300 | 1.5 | Styrene | 1.590 | 30.9 |
| Q | −11.500 | 4.8 | AIR | 1.000 | |
| R | Exit Image Plane | | | | |

*dimensions are in millimeters

Surfaces 425e, 425f of prism 410 are reflecting surfaces. Surface 425e defines an angle ranging from about 18° to about 26° preferably about 22.5° relative to the optical axis while surface 425f defines an angle which ranges from about 4.5° to about 10.5° preferably about 7.5° relative to the optical axis.

The objective lens arrangement produces an inverted image of the object at exit image plane 425r. As indicated in Table 1, the distance from the proximal lens surface 425q of second doublet 424 to exit image plane 425r is about 4.8 mm. The inverted image formed by the objective lens arrangement is subsequently transmitted by relay lens assembly 440.

Referring to FIG. 15, a relay lens module 442 of relay lens assembly 440 is illustrated in detail. Relay lens assembly 440 may include a plurality of relay lens modules, arranged in end to end fashion along the optical axis. Each module 442 is identical with regard to the optical components contained therein, and is capable of transferring an image from an image plane at the entrance side of the module to a successive image plane formed on the exit side. Lens module 442 includes two identical optical assemblies 444 arranged in symmetrical end to end relationship relative to a median plane disposed between the two assemblies. Assemblies 444 are separated by an air gap. Each assembly 444 includes a glass plano cylinder 446 having an adjacent end face and an outer end face relative to the other component in the module. Glass plano cylinder 446 ensures the transfer of a bright image between the modules. Each assembly further includes a single lens 448 bonded to the outer end face of plano cylinder 446 and a single lens 450 bonded to the adjacent end face of the cylinder. Single lens 448, 450 are each preferably a plano-convex lens. The convex surface of lens 448, 450 may be coated with a broad band anti-reflection coating to reduce reflection losses at the air-lens interface. Single lenses 448, 450 are each preferably fabricated from a polymeric material such as an acrylic, polystyrene, polycarbonate, or copolymer styrene-acrylonitrile (SAN). In a preferred embodiment, single lenses 448, 450 are each fabricated from acrylic.

FIG. 15 illustrates ray path and image orientation through lens module 442. The geometrical characteristics of module 442 are defined by an entrance image plane 445a, a front surface 445b, a first bonded surface 445c, a second bonded surface 445d, a first inner surface 445e, a second inner surface 445f, a third bonded surface 445g, a fourth bonded surface 445h, a rear surface 445i and an exit image plane 445j. The geometrical and optical parameters of the module are recorded in Table 2. In Table 2, surfaces A, B–I and J correspond to image plane 445a, surfaces 445b–445i and exit image plane 445j, respectively. Table 2 is as follows.

TABLE 2

| SURFACE | RADIUS | THICK-NESS | MEDIUM | INDEX | ABBE NO. |
|---|---|---|---|---|---|
| A | Entrance Image Plane | 2.5 | AIR | 1.000 | |
| B | 7.350 | 1.4 | Acrylic | 1.492 | 57.4 |
| C | Plano | 24.0 | SF2 | 1.648 | 33.9 |
| D | Plano | 1.5 | Acrylic | 1.492 | 57.4 |
| E | −9.700 | 0.2 | AIR | 1.000 | |
| F | 9.700 | 1.5 | Acrylic | 1.492 | 57.4 |
| G | Plano | 24.0 | SF2 | 1.648 | 33.9 |
| H | Plano | 1.4 | Acrylic | 1.492 | 57.4 |
| I | −7.350 | 2.5 | AIR | 1.000 | |
| J | Exit Image Plane | | | | |

*dimensions are in millimeters

As indicated in Table 2, the distance between entrance image plane 425a and the first lens surface 445b of lens 448 is approximately 2.5 mm. Similarly, the distance between proximal lens surface 445i of lens 448 and exit image plane 445j is also 2.5 mm.

In a preferred embodiment, the relay lens assembly comprises three lens modules aligned in end to end fashion along a common axis.

It is also envisioned that other relay lens assemblies may be incorporated in the optical system of arthroscope 100. Examples of relay lens assemblies which may be adapted for use with arthroscope 100 are disclosed in U.S. Pat. Nos. 4,964,710 to Leiner and 5,188,092 to White and commonly assigned copending U.S. patent application Ser. Nos. 08/132,007 filed Oct. 5 (now U.S. Pat. No. 5,412,504), 1993, 08/132,009 filed Oct. 5, 1993, and 08/120,887 filed Sep. 13, 1993, the contents of each patent and pending application being incorporated herein by reference.

Referring now to FIG. 16, the eye lens assembly of optical system is illustrated in detail. Eye lens assembly 460 includes a doublet lens 462 having two polymeric lens elements 464, 466 which are bonded to each other along adjacent end surfaces. Preferably lens element 464 is a double convex lens and is fabricated from an acrylic while lens element 466 is a meniscus lens and is fabricated from a styrene. The geometrical characteristics of eye lens assembly 460 are defined by entrance image plane 465a, surfaces 465b–d and exit image plane 465. Table 3 below identifies the optical parameters of the eye lens assemblies.

TABLE 3

| SURFACE | RADIUS | THICK-NESS | MEDIUM | INDEX | ABBE NO. |
|---|---|---|---|---|---|
| A | Entrance Plane | 9.1 | AIR | 1.000 | |
| B | 13.500 | 1.8 | Acrylic | 1.492 | 57.5 |
| C | −2.000 | 1.7 | Styrene | 1.590 | 30.9 |
| D | −5.270 | 11.0 | AIR | 1.000 | |
| E | Exit Pupil | | | | |

*dimensions are in millimeters

As indicated in Table 3, the distance between the image plane 465a and the first lens surface 465b of eyelens 462 is approximately 9.1 mm.

It is also contemplated that the view finder or eyepiece assembly 220 having eye lens assembly 460 therein may be connected to a video camera adapter to enable the image to be displaced on a monitor for viewing by the surgical team. It is also possible that the eyepiece assembly 220 may be eliminated so that the optical system is connected directly to the video camera optics.

The optical system of the arthroscope of the present invention provides a clear bright image to the viewer and effectively compensates for predetermined aberrations in the system such as axial chromatic aberration, lateral chromatic aberration and astigmatism. The optical system can be manufactured sufficiently inexpensively to supply the entire arthroscope as a disposable unit. The principle optical components including the prism may be molded of plastic thus further minimizing the cost of the arthroscope. The glass plano cylinder of the relay lens system can also be manufactured cost effectively.

To the extent not already indicated, it also will be understood by those of ordinary skill in the art that any one of various specific embodiments herein described and illustrated may be further modified to incorporate features shown in other of the specific embodiments.

The invention in its broader aspects therefor is not limited to the specific embodiments herein shown and described but departures may be made therefrom within the scope of the accompanying claims without department from the principles of the invention and without sacrificing its chief advantages.

What is claimed is:

1. A disposable rigid arthroscope which comprises:

a frame member;

an outer tube member extending distally from said frame member and defining a longitudinal axis;

an inner lens tube member disposed within said outer tube member;

optical means disposed within said inner lens tube member for conveying an image of an object, said optical means defining an optical axis and including an objective lens arrangement disposed adjacent a distal end portion of said inner lens tube member, said objective lens arrangement including means for altering the field of view of said optical means with respect to said optical axis of said optical means;

an illumination system including a plurality of optical fibers disposed within a space defined between said outer tube member and said inner lens tube member; and a generally arcuate shim member disposed about at least a peripheral portion of said distal end portion of said inner lens tube member, said shim member including first and second opposed side edges angularly oriented relative to said optical axis, said first and second side edges configured and dimensioned to orient end portions of at least a group of said optical fibers at a general angular orientation relative to said optical axis in the general direction of the field of view, said shim member having a proximal end portion extending on both sides thereof along an inner periphery of said outer tube member so as to define a major cross-sectional dimension, said major cross-sectional dimension approximating a maximum inner dimension of said outer tube member such that said shim member engages said outer tube member and stabilizes said inner lens tube member within said outer tube member thereby facilitating assembly of said inner lens tube member therewithin.

2. The disposable rigid arthroscope according to claim 1, wherein said first side edge of said shim member defines a first guiding surface to position and orient end portions of a first group of said optical fibers at a general angular orientation relative to said optical axis in the general direction of the field of view, and wherein said second side edge defines a second guiding surface to orient end portions of a second group of said optical fibers at a general angular orientation relative to said optical axis in the general direction of the field of view.

3. The disposable rigid arthroscope according to claim 2, wherein said inner lens tube member defines an oblique distal end face.

4. The disposable rigid arthroscope according to claim 3, wherein said distal end face of said inner lens tube member includes a curved lip portion, said curved lip portion disposed at an upper portion of said distal end face and defining an outer peripheral surface angularly oriented relative to said optical axis, said outer peripheral surface orienting end portions of a third group of said optical fibers at a generally angular orientation relative to said optical axis in the general direction of the field of view.

5. The disposable rigid arthroscope according to claim 4, wherein said shim member is disposed about a lower peripheral portion of said inner lens tube member.

6. The disposable rigid arthroscope according to claim 5, wherein said inner lens tube is eccentrically disposed within said outer tube member.

7. The disposable rigid arthroscope according to claim 6, wherein said end portions of said optical fibers are disposed in an opening defined between said outer tube member, said inner lens tube member and said arcuate shim member, and further wherein said end portions of said optical fibers define a generally crescent shaped array in cross-section.

8. The disposable rigid arthroscope according to claim 3, wherein said oblique distal end face defines an angle of about 30° relative to said optical axis.

9. The disposable rigid arthroscope according to claim 2 wherein said inner lens tube member and said outer tube member are each generally cylindrically-shaped.

10. The disposable rigid arthroscope according to claim 9, wherein said shim member has a proximal end portion defining a generally semicircular shape in cross section.

11. The disposable rigid arthroscope according to claim 10, wherein said semi-circular proximal end portion of said shim member defines a diameter approximating an inner diameter of said outer tube member such that said proximal end portion of said shim member engages said outer tube member to stabilize said inner lens tube member within said outer tube member.

12. The disposable rigid arthroscope according to claim 2, wherein said shim member is generally annular in shape and is disposed about the periphery of said distal end portion of said inner tube member, said upper portion defining an outer positioning surface angularly oriented relative to said optical axis to orient end portions of a third group of said optical fibers in a general angular orientation relative to said optical axis in the general direction of the field of view.

13. The disposable rigid arthroscope according to claim 1, wherein said frame member includes a light guide connector for connecting a light guide to said illumination system of the arthroscope.

14. The disposable rigid arthroscope according to claim 13, wherein said light guide connector includes an illuminator coupler disposed therein, said illuminator coupler comprising a light transmissive element for transmitting light received from a light guide to said illumination system, said light transmissive element defining a first entry side adjacent the light guide and a second exit side adjacent said illumination system, said first entry side defining a first cross-sectional dimension and said second exit side defining a second cross-sectional dimension, and wherein said first cross-sectional dimension is greater than said second cross-sectional dimension.

15. The disposable rigid arthroscope according to claim 14, wherein said first cross-sectional dimension of said light transmissive element approximates an illuminating aperture of the light guide and wherein said second cross-sectional dimension approximates an illuminating aperture of said illumination system of the arthroscope.

16. The disposable rigid arthroscope according to claim 15, wherein said light transmissive element is generally frustoconically shaped.

17. The disposable rigid arthroscope according to claim 16, wherein said light transmissive element comprises a molded polymeric material.

18. The disposable rigid arthroscope according to claim 17, wherein said illuminating coupler comprises a support member, said light transmissive element being supported within said support member.

19. The disposable rigid arthroscope according to claim 1, wherein said means for altering the angle of view of said optical means comprises a molded polymeric prism.

20. The disposable rigid arthroscope according to claim 19, wherein said objective lens arrangement further comprises a distal cover element disposed at said distal end face of said inner lens tube member and a plurality of lens elements adjacent said prism.

21. The disposable rigid arthroscope according to claim 20, wherein said distal cover element and said prism are connected to each other along adjacent end faces.

22. The disposable rigid arthroscope according to claim 21, wherein means is provided for positively positioning said distal cover element and said prism in said inner lens tube member.

23. The disposable rigid arthroscope according to claim 22, wherein said positioning means comprises a curved lip portion disposed at an upper portion of said distal end face of said inner lens tube member, said curved lip portion defining an inner peripheral surface configured and dimensioned to engage an outer edge portion of said distal cover element to assist in retaining said distal cover element and said prism in a predetermined position within said inner lens tube member.

24. The disposable rigid arthroscope according to claim 23, wherein said objective lens arrangement is characterized by the following data:

| SURFACE | RADIUS | THICK-NESS | MEDIUM | INDEX | ABBE NO. |
|---|---|---|---|---|---|
| A | Object Plane | (Object Distance) | AIR | 1.000 | |
| B | Plano | 0.7 | Styrene | 1.590 | 30.9 |
| C | 0.800 | 0.7 | AIR | 1.000 | |
| D | −1.100 | 1.0 | Styrene | 1.590 | 30.9 |
| E | Plano | 1.4 | Styrene | 1.590 | 30.9 |
| F | Plano | 1.4 | Styrene | 1.590 | 30.9 |
| G | Plano | 0.2 | AIR | 1.000 | |
| H | 19.763 | 1.0 | Styrene | 1.590 | 30.9 |
| I | 1.500 | 1.9 | Acrylic | 1.492 | 57.4 |
| J | −2.062 | 0.3 | Air | 1.000 | |
| K | 4.132 | 2.5 | Acrylic | 1.492 | 57.4 |
| L | −1.500 | 1.0 | Styrene | 1.590 | 30.9 |
| M | 4.000 | 1.4 | Acrylic | 1.492 | 57.4 |
| N | 2.304 | 0.6 | AIR | 1.000 | |
| O | 2.391 | 2.0 | Acrylic | 1.492 | 57.4 |
| P | −4.300 | 1.5 | Styrene | 1.590 | 30.9 |
| Q | −11.500 | 4.8 | AIR | 1.000 | |
| R | Exit Image Plane | | | | |

*dimensions are in millimeters

25. The disposable rigid arthroscope according to claim 19, wherein said optical means comprises a relay lens arrangement for transferring an image formed by said objective lens arrangement.

26. The disposable rigid arthroscope according to claim 25, wherein said relay lens arrangement comprises at least one relay lens module characterized by the following data:

| SURFACE | RADIUS | THICK-NESS | MEDIUM | INDEX | ABBE NO. |
|---|---|---|---|---|---|
| A | Entrance Image Plane | 2.5 | AIR | 1.000 | |
| B | 7.350 | 1.4 | Acrylic | 1.492 | 57.4 |
| C | Plano | 24.0 | SF2 | 1.648 | 33.9 |
| D | Plano | 1.5 | Acrylic | 1.492 | 57.4 |
| E | −9.700 | 0.2 | AIR | 1.000 | |
| F | 9.700 | 1.5 | Acrylic | 1.492 | 57.4 |
| G | Plano | 24.0 | SF2 | 1.648 | 33.9 |
| H | Plano | 1.4 | Acrylic | 1.492 | 57.4 |

-continued

| SURFACE | RADIUS | THICKNESS | MEDIUM | INDEX | ABBE NO. |
|---------|--------|-----------|--------|-------|----------|
| I | −7.350 | 2.5 | AIR | 1.000 | |
| J | Exit Image plane | | | | |

*dimensions are in millimeters

27. The disposable rigid arthroscope according to claim 25, wherein said optical means further comprises an eye lens arrangement for viewing an image transferred by said relay lens arrangement, said eye lens arrangement comprising at least one polymeric lens.

28. The disposable rigid arthroscope according to claim 27, wherein said eye lens arrangement is characterized by the following data:

| SURFACE | RADIUS | THICKNESS | MEDIUM | INDEX | ABBE NO. |
|---------|--------|-----------|--------|-------|----------|
| A | Image Plane | 9.1 | AIR | 1.000 | |
| B | 13.500 | 1.8 | Acrylic | 1.492 | 57.5 |
| C | −2.000 | 1.7 | Styrene | 1.590 | 30.9 |
| D | −5.270 | 11.0 | AIR | 1.000 | |
| E | Exit Pupil | | | | |

*dimensions are in millimeters

29. A disposable rigid arthroscope which comprises:
a generally cylindrically-shaped outer sleeve member;
a generally cylindrically-shaped inner lens tube member disposed eccentrically within said outer sleeve member and defining a longitudinal axis;
an optical system disposed within said inner lens tube member for forming and transferring an image of an object, said optical system defining an optical axis in general parallel alignment with said longitudinal axis of said inner lens tube member, said optical system including means for providing a visual field direction which is angularly offset relative to said optical axis;
a plurality of optical fibers disposed within a space defined between said outer sleeve member and said inner lens tube member wherein end portions of said optical fibers are angularly offset relative to said optical axis to direct light in the visual field direction; and
an arcuate shim member disposed about a lower distal peripheral portion of said inner lens tube member, said shim member having a proximal end portion defining a generally semicircular shape and having first and second side edges, said first and second side edges angularly offset relative to said optical axis and supporting end portions of said optical fibers in the angularly offset relationship relative to said optical axis, said proximal end portion of said shim member extending on both sides thereof along an inner periphery of said outer sleeve member so as to define a major cross-sectional dimension, said major cross-sectional dimension approximating an inner diameter of said outer sleeve member such that said proximal end portion of said shim member engages said outer sleeve member to stabilize said inner lens tube member within said outer sleeve member to thereby facilitate mounting of said inner lens tube member therewithin.

30. The disposable rigid arthroscope according to claim 29, wherein said inner lens tube member includes an oblique distal end face, said oblique distal end face including an upper lip portion curved towards said longitudinal axis of said inner lens tube member, said curved upper lip portion defining a peripheral guiding surface angularly offset relative to said optical axis to orient end portions of said optical fibers in the angular offset arrangement relative to said optical axis to direct light in the visual field direction.

31. In an endoscope having an inclined angle of view, the endoscope including an outer tube member, an inner lens tube member disposed within said outer tube member, optical means disposed within said inner lens tube member for conveying an image of an object and having means for providing a visual field direction which is angularly offset relative to an optical axis of said optical means and an illumination system including a plurality of optical fibers, wherein the improvement comprises an annular shim member positioned about a distal end portion of said inner lens tube member, said annular shim member defining first and second side edges, said first side edge defining a first guiding surface to position and orient end portions of a first group of said optical fibers at a general angular orientation relative to said optical axis in the general direction of the field of view, said second side edge defining a second guiding surface to orient end portions of a second group of said optical fibers at a general angular orientation relative to said optical axis in the general direction of the field of view, said shim member having a proximal end portion extending on both sides thereof along an inner periphery of said outer tube member so as to define a major cross-sectional dimension, said major cross-sectional dimension approximating a maximum inner dimension of said outer tube member such that said shim member engages inner wall portions of said outer tube member to stabilize said inner lens tube member therewithin.

32. The endoscope according to claim 31 wherein said shim member has an upper portion, said upper portion defining an outer positioning surface angularly oriented relative to said optical axis to orient end portions of a third group of said optical fibers in a general angular orientation relative to said optical axis in the general direction of the field of view.

* * * * *